United States Patent [19]
Millis

[11] Patent Number: 6,136,985
[45] Date of Patent: Oct. 24, 2000

[54] CLA ESTERS AND USES THEREOF

[75] Inventor: James R. Millis, Kohler, Wis.

[73] Assignee: DCV, Inc., Wilmington, Del.

[21] Appl. No.: 09/217,173

[22] Filed: Dec. 21, 1998

Related U.S. Application Data

[60] Provisional application No. 60/068,615, Dec. 23, 1997.

[51] Int. Cl.$^7$ ............ A61K 7/42; C07D 335/04; C07D 311/04; C07D 311/74
[52] U.S. Cl. ............ 549/23; 549/398; 549/407; 549/408; 549/410; 424/59
[58] Field of Search ............ 549/23, 410, 408, 549/407, 398; 424/59

[56] References Cited

U.S. PATENT DOCUMENTS

| | | | |
|---|---|---|---|
| 4,393,043 | 7/1983 | Koulbanis et al. | 424/59 |
| 4,552,897 | 11/1985 | Asato et al. | 514/554 |
| 4,649,158 | 3/1987 | Asato et al. | 514/554 |
| 4,997,958 | 3/1991 | Pauling et al. | 549/315 |
| 5,017,614 | 5/1991 | Pariza et al. | 514/558 |
| 5,136,055 | 8/1992 | Tramount | 549/266 |
| 5,208,356 | 5/1993 | Pariza et al. | 554/79 |
| 5,234,702 | 8/1993 | Katz et al. | 426/72 |
| 5,288,619 | 2/1994 | Brown et al. | 435/134 |
| 5,391,373 | 2/1995 | Mausner | 424/401 |
| 5,545,407 | 8/1996 | Hall et al. | 424/401 |
| 5,593,682 | 1/1997 | Papas et al. | 424/401 |
| 5,654,181 | 8/1997 | Oester et al. | 435/135 |
| 5,658,580 | 8/1997 | Mausner | 424/401 |
| 5,690,918 | 11/1997 | Jacks et al. | 424/64 |

FOREIGN PATENT DOCUMENTS

| | | |
|---|---|---|
| 296483 | of 1988 | European Pat. Off. . |
| 57-193473 | 11/1982 | Japan . |
| WO 97/18320 | of 1997 | WIPO . |
| WO 97/26003 | of 1997 | WIPO . |
| WO97/22328 | of 1997 | WIPO . |
| WO 99/26588 | of 1999 | WIPO . |

OTHER PUBLICATIONS

Chemical Abstracts 126:94623, Nichols, 1996.
Chemical Abstracts 125:230206, Punto, 1996.
CA 125:204084, Wang, 1994.
CA 125:143085. Yvergnaux, 1996.
CA 125:L123295, Cohen, 1996.
Arcos et al., *Biotechnology Letters*, 20(6):617–621 (1998).
Chen et al., *J. Org. Chem.*, 63:9620–9621 (1998).
Garcia et al., *Biotechnology Letters*, 20:393–395 (1998).
Humeau et al., *Biotechnology Letters*, 17(10):1091–1094 (1995).
Praill, *J. Chem. Soc.*, Part III:3100–3101 (1959).
Spassow, *Chem. Ber.*, 75:779–780 (1942).
Wagner, et al., *Synthetic organic chemistry*, John Wiley & Sons, Inc., New York, (1953).

*Primary Examiner*—D. Margaret Seaman
*Attorney, Agent, or Firm*—Sheridan Ross P.C.

[57] ABSTRACT

The present invention provides CLA esters and uses thereof. More particularly, the present invention provides a composition for topical use comprising CLA esters and a topical carrier. In addition, the present invention specifically provides tocopheryl CLA esters, ascorbyl CLA esters and retinyl CLA esters.

26 Claims, No Drawings

CLA ESTERS AND USES THEREOF

CROSS-REFERENCE TO RELATED APPLICATIONS

This application claims the benefit of U.S. Provisional Patent Application Ser. No. 60/068,615, filed Dec. 23, 1997.

FIELD OF THE INVENTION

The present invention is directed to a novel CLA esters and uses thereof. Specifically, the present invention is directed to esters of conjugated linoleic acid and esters of conjugated linolenic acid and the use thereof in cosmetic and dermatological compositions.

BACKGROUND OF THE INVENTION

The term "CLA" is a generic term used to reference both conjugated linoleic acid and conjugated linolenic acid. CLA is a recognized nutritional supplement and an effective inhibitor of epidermal carcinogenesis and forestomach neoplasia in mice, and of carcinogen-induced rat mammary tumors. CLA has been shown to prevent adverse effects caused by immune stimulation in chicks, mice and rats, and has been shown to decrease the ratio of low density lipoprotein cholesterol to high density lipoprotein cholesterol in rabbits fed an atherogenic diet. CLA also reduces body fat in mouse, rat, chick, and pig models. CLA has also been shown to be effective in treating skin lesions when included in the diet.

Vitamins are essential nutrients which are present in natural food stuffs or sometimes are produced within the body. The importance of vitamins is well recognized. Among their many activities, vitamins are recognized for their activity as coenzymes and precursors of coenzymes in the regulation of many body functions including metabolic processes. Vitamin A possesses, inter alia, anti-infective, antixerophthalmic properties. Vitamins C and E possess antioxidant activities and may be effective in preventing diseases such as cold, cancer and variety of other illnesses. Vitamin E belongs to a class of compounds known as tocopherols. All tocopherols contain a chroman ring moiety and are naturally-occurring compounds that possess an antioxidant activity.

A need exists in the field of compositions useful in topical application and in nutrition for improved compositions and formulations having improved activity, such as compositions having multiple activities. For example, compositions having complementary activities, synergistic activities, and/or active components in physiologically useful ratios provide significant advancements in the field.

SUMMARY OF THE INVENTION

The present invention provides a composition for topical application comprising a CLA ester and a topical carrier. Preferably, the CLA ester is selected from the group consisting of tocopheryl CLA, ascorbyl CLA, retinyl CLA, and mixtures thereof. More preferably, the CLA ester is selected from the group consisting of tocopheryl 9,11-linoleate, tocopheryl 10,12-linoleate, tocopheryl 9,11,15-linolenate, tocopheryl 10,12,15-linolenate, ascorbyl 9,11-linoleate, ascorbyl 10,12-linoleate, ascorbyl 9,11,15-linolenate, ascorbyl 10,12,15-linolenate, retinyl 10,12-linoleate, retinyl 9,11,15-linolenate, retinyl 10,12,15-linolenate, and mixtures thereof.

In a preferred embodiment, the topical composition comprising CLA ester is a cosmetic composition. The cosmetic composition can further comprise a sun block or a wax.

In another preferred embodiment, the topical composition comprising CLA ester is a dermatological composition. The dermatological composition can further comprise benzoyl peroxide.

Another embodiment of the present invention is a compound of the formula:

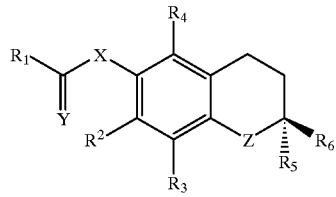

wherein X, Y and Z are independently O, S, or $NR_7$, preferably X, Y and Z are O.

$R_1$ is $C_4$–$C_{30}$ conjugated polyene.

$R_2$, $R_3$, and $R_4$ are independently hydrogen or $C_1$–$C_6$ alkyl.

$R_5$ and $R_6$ are independently hydrogen or $C_1$–$C_{20}$ alkyl.

$R_7$ is hydrogen, $C_1$–$C_6$ alkyl or a protecting group for an amide nitrogen, an amine nitrogen or an imine nitrogen.

Yet another embodiment of the present invention is a compound of the formula:

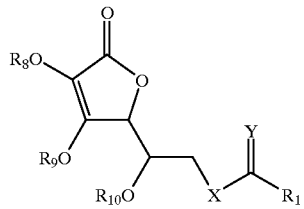

wherein X and Y are independently O, S or $NR_7$. Preferably, X and Y are O. $R_8$, $R_9$, $R_{10}$ are independently hydrogen or a hydroxy protecting group. Preferably, $R_8$, $R_9$, $R_{10}$ are hydrogen.

Yet another embodiment of the present invention is a compound of the formula:

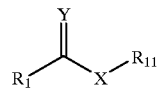

wherein X and Y are independently O, S, or $NR_7$. Preferably, $R_7$ is hydrogen or an amide nitrogen protecting group. $R_{11}$ is $C_4$–$C_{30}$ conjugated polyene.

DETAILED DESCRIPTION OF THE INVENTION

The present invention provides a composition for topical application comprising a conjugated polyene ester and a topical carrier. Preferably, the conjugated polyene ester is CLA ester. As used in this invention, "CLA" refers to conjugated linoleic acid, conjugated linolenic acid and salts thereof. As used in this invention, "conjugated" refers to a presence of a non-aromatic carbon atom having a double or a triple bond that is attached to another carbon atom that is not sp³-hybridized or to an atom having a lone pair of electrons. Exemplary CLA include, but not limited to, 9,11-linoleic acid; 10,12-linoleic acid; 9,11,15-linolenic acid; 10,12,15-linolenic acid; and salts thereof. The configuration of the double bonds present in CLA can be all cis-, all trans-, or mixtures thereof.

The CLA ester useful in topical application compositions of the present invention is selected from the group consisting of tocopheryl CLA, ascorbyl CLA, retinyl CLA, and mixtures thereof. Preferably, the CLA ester is selected from the group consisting of tocopheryl 9,11-linoleate, tocopheryl 10,12-linoleate, tocopheryl 9,11,15-linolenate, tocopheryl 10,12,15-linolenate, ascorbyl 9,11-linoleate, ascorbyl 10,12-linoleate, ascorbyl 9,11,15-linolenate, ascorbyl 10,12,15-linolenate, and mixtures thereof. More preferably, the CLA ester is selected from the group consisting of tocopheryl (Z,E)-9,11-linoleate, tocopheryl (E,Z)-10,12-linoleate, tocopheryl (Z,E,E)-9,11,15-linolenate, tocopheryl (E,Z,E)-10,12,15-linolenate, ascorbyl (Z,E)-9,11-linoleate, ascorbyl (E,Z)-10,12-linoleate, ascorbyl (Z,E,E)-9,11,15-linolenate, ascorbyl (E,Z,E)-10,12,15-linolenate, retinyl (Z,E)-9,11-linoleate, retinyl (E,Z)-10,12-linoleate, retinyl (Z,E,E)-9,11,15-linolenate, retinyl (E,Z,E)-10,12,15-linolenate, and mixtures thereof.

The term "topical carrier", as used herein, is well-known to one of ordinary skill in the art, and means one or more compatible solid or liquid filler diluents or vehicles which are suitable for facilitating topical application of an active compound to a biological subject. A "biological subject" refers to any animal including a human, and preferably, refers to a human. The term "compatible", as used herein, means that the component or components of the topical carrier are capable of being commingled with the other components of the composition of the present invention, and with each other, in a manner such that there is no interaction which would substantially reduce the therapeutic efficacy of the composition under ordinary use situations. The topical carrier can be a pharmaceutically acceptable carrier. The term "pharmaceutically-acceptable", as used herein, means that the topical carrier must of sufficiently high purity and suitable for use in contact with the skin of a biological subject without undue toxicity, incompatibility, instability, allergic response, and the like.

The composition for topical application of the present invention is administered topically to a biological subject, i.e., by the direct laying on or spreading of the composition on the skin of the subject. Preferably, the compositions for topical application useful in the present invention involve compositions suitable for topical application to human skin.

The composition for topical application (i.e., topical composition) useful in the present invention can be made into a variety of product types. These include, but are not limited to, lotions, creams, gels, sticks, sprays, ointments, pastes, mousses, and cosmetics. These product types can comprise several types of carrier systems including, but not limited to, solutions, emulsions, gels, solids, and liposomes. Also useful are cleansing compositions which also deliver the components of the present invention to the skin during the cleansing process.

A topical composition useful in the present invention formulated as a solution carrier system typically includes a pharmaceutically-acceptable aqueous or organic solvent. Water is a preferred solvent. Exemplary suitable organic solvents include ethanol, propylene glycol, polyethylene glycol, polypropylene glycol, glycerol, 1,2,4-butanetriol, sorbitol esters, 1,2,6-hexanetriol, isopropanol, butanediol, and mixtures thereof.

If the topical composition useful in the present invention is formulated as an aerosol carrier system and applied to the skin as a spray-on, a propellant is added to a solution composition. Exemplary propellants include chlorofluorinated lower molecular weight hydrocarbons. Other useful propellants are discussed in Sagarin, *Cosmetics Science and Technology*, 2nd Ed., 1972, Vol. 2, ("Sagarin volume 2"), which is incorporated herein in its entirety. Useful propellants are disclosed in pages 443–465 of Sagarin, volume 2.

The topical composition of the present invention can be formulated as a solution carrier system comprising an emollient. Such compositions contain from about 2% to about 50% of a topical pharmaceutically-acceptable emollient. As used herein, "emollient" refers to materials used for the prevention or relief of dryness, as well as for the protection of the skin. A wide variety of suitable emollients are known and can be used herein. See e.g., Sagarin, *Cosmetics Science and Technology*, 2nd Ed., 1972, Vol. 1, ("Sagarin volume 1") and U.S. Pat. No. 4,919,934, to Deckner et al., issued Apr. 24, 1990, both of which are incorporated herein by reference in their entirety. Suitable emollients are disclosed on pages 32–43 of Sagarin volume 1.

A lotion can be made from a solution carrier system. Lotions comprise from about 1% to about 20% emollient, and from about 50% to about 90% water.

Another type of product that can be formulated from a solution carrier system is a cream. A cream typically comprises from about 5% to about 50% of an emollient, and from about 45% to about 85% water.

Yet another type of product that can be formulated from a solution carrier system is an ointment. An ointment can comprise a simple base of animal or vegetable oils or semi-solid hydrocarbons (oleaginous). Ointments can also comprise absorption ointment bases which absorb water to form emulsions. Ointment carriers can also be water soluble. An ointment can comprise from about 2% to about 10% of emollient and from about 0.1% to about 2% of a thickening agent.

The composition for topical application of the present invention can further comprise ancillary components. The ancillary components, whose use is optional but preferably, impart additional desirable properties to the composition for topical application of the present invention. These ancillary components can include a thickener component, a preservative component, a lipid-soluble component, fragrance, a sun block, wax, and coloring.

The thickener component can comprise at least one of xanthan gum and carrageenan. A more complete disclosure of thickening agents useful herein can be found on pages 72–73 of Sagarin volume 1.

The topical composition can further comprise a preservative component to retard microbial and mold growth in the composition, which is typically manufactured under clean but non-sterile conditions. A useful preservative component includes propylene glycol, phenoxyethanol, chlorphenesin, methylparaben, ethylparaben, butylparaben, propylparaben, and mixtures thereof.

The composition for topical application can further include a lipid-soluble component that provide added smoothness. The lipid-soluble component include, but are not limited to, steareth-2, steareth-21, dimethicone and a branched chain neopentanoate ester such as octyldodecyl neopentanoate, heptyldodecyl neopentanoate, nonyldodecyl neopentanoate, octylundecyl neopentanoate, heptylundecyl neopentanoate, nonylundecyl neopentanoate, octyltridecyl neopentanoate, heptyltridecyl neopentanoate, and nonyltridecyl neopentanoate. Steareth-2 is polyoxyethylene (2) stearyl ether with 0.01% butylated hydroxyanisole and 0.005% citric acid added as preservatives. Similarly, steareth-21 is polyoxyethylene (21) stearylether with 0.01% butylated hydroxyanisole and 0.005% citric acid added as preservatives.

The composition for topical application of the present invention can further comprise fragrance. The fragrance used is a conventional cosmetic fragrance chosen to impart the desired olfactory properties to the composition. The use of fragrance is well-known in the cosmetic art.

The composition for topical application of the present invention can further comprise a sun block. Types of compounds which are effective as a sun block are well known by one skilled in the art of cosmetics.

The topical composition of the present invention can also comprise a wax. The type of wax used depends on the nature of the topical composition product. For example, one skilled in the art of cosmetics knows which type of wax is useful in formulating a topical composition of the present invention as a lipstick, facial cream or other cosmetic products.

The composition used in topical application of the present invention can further comprise coloring to give the composition an aesthetically desirable appearance. The use of coloring agents is well known in the cosmetics art.

The topical composition of the present invention can be used as a cosmetic composition, such as a non-drying lipstick, or a skin cream. The topical composition will have useful utilities derived from its component parts. For example, it will have an anti-oxidant and an anti-inflammatory properties derived from vitamin C or E. It will reduce UV-induced damage to skin, inhibit premature aging of the skin and minimize degradation caused by free radicals. It can also have properties associated with a conjugated polyene (e.g., CLA) including anti-tumor properties, enhancement of immune response and ability to reduce body fat.

The topical composition of the present invention can be easily absorbed through skin, and as such it is useful as a moisturizer to help relieve dry skin or to treat skin lesions. When used in conjunction with benzoyl peroxide to obtain the benefit of anti-bacterial effect, the moisturizing capability of the topical composition can reduce the irritation normally associated with benzoyl peroxide.

In a preferred embodiment, the topical composition of the present invention is a cosmetic composition. Uses of the present composition as a cosmetic composition include, but are not limited to, skin-cream, lipstick, lotion, and cleansing cream. Examples of making a skin-cream are disclosed, for example, by Mausner in U.S. Pat. No. 5,658,580, issued Aug. 19, 1997, and in U.S. Pat. No. 5,391,373, issued Feb. 21, 1995, which are incorporated herein in their entirety. An example of making a lipstick is disclosed by Jacks et al. in U.S. Pat. No. 5,690,918, issued Nov. 25, 1997, which is incorporated herein in its entirety.

In another preferred embodiment, the composition for topical application of the present invention is a dermatological composition. The dermatological composition can further comprise an active ingredient such as benzoyl peroxide, tetracycline or other therapeutically effective ingredients.

The dermatological composition can be used to treat skin lesions, acne or other dermatologically related ailments. When benzoyl peroxide is present in the dermatological composition, the composition of the present invention provides reduction in irritation of skin due to the presence of benzoyl peroxide.

Another embodiment of the present invention provides a compound derived from a conjugated polyene and a chroman. Specifically, the compound of the present invention is of the formula:

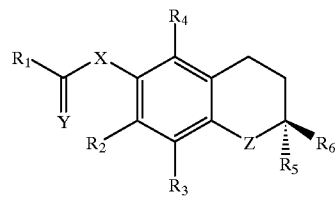

I wherein X, Y and Z are independently O, S, or $NR_7$, preferably X, Y and Z are O.

$R_1$ is $C_4$–$C_{30}$ conjugated polyene. As used in this invention, a "conjugated polyene" refers to a moiety having two or more unsaturated bonds such as a double bond, a triple bond or a combination thereof that are conjugated. It will be appreciated that when a conjugated polyene contains more than two unsaturated bonds, not all unsaturated bonds need to be conjugated. Preferably $R_1$ is selected from the group consisting of a conjugated heptadecadienyl and a conjugated heptadecatrienyl. More preferably, $R_1$ is selected from the group consisting of 8,10-heptadecadienyl, 9,11-heptadecadienyl, 8,10,14-heptadecatrienyl, 9,11,14-heptadecatrienyl, and mixtures thereof. And most preferably, R1 is selected from the group consisting of (Z,E)-8,10-heptadecadienyl, (E,Z)-9,11-heptadecadienyl, (Z,E,E)-8,10,14-heptadecatrienyl, (E,Z,E)-9,11,14-heptadecatrienyl, and mixtures thereof.

$R_2$, $R_3$, and $R_4$ are independently hydrogen or $C_1$–$C_6$ alkyl. Alkyl groups according to the invention are aliphatic hydrocarbons which can be straight or branched chain groups. Alkyl groups optionally can be substituted with one or more substituents, such as halo, aryl, hydroxy, alkoxy, carboxy, oxo and cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, n-pentyl, acetyl, propionyl, pivaloyl, and hexyl. Preferably $R_2$, $R_3$, and $R_4$ are independently hydrogen or methyl. Preferably $R_7$ is hydrogen.

$R_7$ is hydrogen, $C_1$–$C_6$ alkyl or a protecting group for an amine nitrogen, an amide nitrogen or an imine nitrogen. A variety of protecting groups are known in the art, and can be employed. Examples of many of the possible protecting groups can be found in *Protective Groups in Organic Synthesis*, 2nd edition, T. H. Greene and P. G. M. Wuts, John Wiley & Sons, New York, 1991, which is incorporated herein in its entirety.

$R_5$ and $R_6$ are independently hydrogen or $C_1$–$C_{20}$ alkyl. Preferably, $R_5$ and $R_6$ are independently methyl or 4,8,12-trimethyltridecyl.

In a preferred embodiment of the present invention, $R_1$ is (Z,E)-8,10-heptadecadienyl, $R_2$, $R_3$, $R_4$ and $R_5$ are methyl, and $R_6$ is 4,8,12-trimethyltridecyl.

In another preferred embodiment of the present invention, R, is (E,Z)-9,11-heptadecadienyl, R2, $R_3$, $R_4$ and $R_5$ are methyl, and $R_6$ is 4,8,12-trimethyltridecyl.

A compound (I) of the present invention can be prepared from a condensation reaction (i.e., an esterification reaction including chemical and enzymatic esterification reactions) between a CLA and tocopherol using standard esterification reaction conditions. For example, a mixture of a CLA and tocopherol can be stirred in the presence of an acid catalyst or an esterification enzyme, such as lipase, to produce a tocopheryl CLA ester. Exemplary lipases useful in preparation of CLA esters include *Candida antartica* (Novozym 435®, Novo Nordisk Biochem North America, Inc., Franklinton, N.C.), *Muco miehei* (Lipozyme IM-60®, Novo Nordisk Biochem North America, Inc.), *Candida cylindracea* (Amano AY®, Amano Enzyme U.S.A., Lombard, Ill.), *Pseudomonas cepacia* (Amano PS®, Amano Enzyme U.S.A.), *Pseudomonas fluorescens, Candida rugosa, Aspergillus niger, Geotrichum candidum*, and other microbial lipases known to one of ordinary skill in the art. The esterification reaction can also be conducted by a continuous removal of water that is formed during the reaction. This removal of water provides a higher yield of the desired tocopheryl CLA ester.

As used in this invention, "tocopherol" refers to any of the tocopherol compound including α-tocopherol (i.e., vitamin E), β-tocopherol, γ-tocopherol, δ-tocopherol, ε-tocopherol, η-tocopherol, $\zeta_1$-tocopherol, $\zeta_2$-tocopherol and mixtures thereof.

A compound (I) of the present invention can also be synthesized from a reaction between an acid anhydride or an acyl chloride of CLA and tocopherol. A method for preparing an acid anhydride or acyl chloride of CLA is well known to one skilled in the art of organic chemistry.

Any of the methods for preparing tocopheryl linoleate can also be used to prepare a compound of the present invention. A synthesis of tocopheryl linoleate is disclosed by Koho, Japanese Patent Application No. 57,193,473, PCT Application No. WO 92/211,670, Praill, *J. Chem. Soc.*, 1959, 3100 and Ashirova et al., Khim.-Farm. Zn., 1987, 21, 210, which are incorporated by reference herein in their entirety.

CLA can be obtained by isolation, chemical synthesis or isomerization of linoleic acid or linolenic acid. Linoleic acid and/or linolenic acid can be converted to CLA by chemical methods, or by enzymatic isomerization using an isomerase enzyme. An isomerase enzyme such as 9,11-isomerase can be isolated from *Lactobacillus reuteri* (e.g., ATCC 23272), *B. subtilis, B. licheniformis* and other organisms that produce an isomerase enzyme which is useful in converting linoleic acid and/or linolenic acid to CLA. Such organism may be a mutant form or a genetically altered form to produce the desired isomerase. A chemical method of converting linoleic acid and/or linolenic acid to CLA is disclosed in American Oil Chemists' Society Official Method Cd 7–58, pages 1–11, American oil chemists' society, Champaign, Ill. (1973) which is incorporated herein its entirety. CLA can also be The salts of the CLA can be made by reacting the acids with a base. Natural CLA can also be prepared from linoleic acid by the biological action of an isomerase such as $\Delta^{12}$-cis, $\Delta^{11}$-transisomerase. See for example, Kepler et al., *J. B. C.*, 1970, 245, 3612, Kemp et al., *J. Gen. Microbiol.*, 1975, 90, 100, Mills et al., *Aust. J. Biol. Sci.*, 1970, 23, 1109, Verhulst et al., *FEMS Microbiol. Ecol.*, 1985, 31, 255, Fujimoto et al., *Biosci. Biotech. Biochem.*, 1993, 57, 1026, and Eyssen and Verhulst, *Appl. Environ. Microbiol.*, 1984, 47, 39, which are incorporated herein in their entirety. Conjugated linoleic acid can also be obtained by fermentation including from bacteria such as *Lactobacillus reuteri*, and a cell line which has been genetically engineered. See for example, PCT Publication No. WO 96/38137, which is incorporated herein in its entirety.

Tocopherols can be purchased from a variety of chemical companies including Aldrich Chemical Company (Milwaukee, Wis.). Tocopherols can also be purified from vegetable oils or prepared by complete chemical synthesis. See generally, Kirk-Othmer Encyclopedia of Chemical Technology, volume 24, pages 214–227 (3rd ed. 1984), which is incorporated herein in its entirety.

In addition to other uses discussed above, tocopheryl CLA esters can also be used as a dietary supplement. Both tocopherol and CLA are dietary nutrients. Tocopheryl CLA ester is converted into tocopherol and CLA in the body; thus, tocopheryl CLA ester supplies both necessary dietary nutrients in one compound. The recommended amount of both tocopherol and CLA can be satisfied by an appropriate amount of tocopheryl CLA ester compound.

Another embodiment of the present invention provides a compound of the formula II.

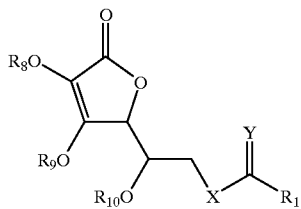

II wherein preferably X and Y are O. Preferably, in a compound of the formula II, $R_8$, $R_9$, and $R_{10}$ are independently H or a hydroxy protecting group. A variety of hydroxy protecting group is also disclosed in the above referenced and incorporated book entitled *Protective Groups in Organic Synthesis*, 2nd edition, by T. H. Greene and P. G. M. Wuts. Preferably the hydroxy protecting group is an acetyl moiety (—C(O)CH$_3$). More preferably $R_8$, $R_9$, and $R_{10}$ are H.

The compound of formula II can be obtained by a reaction between ascorbic acid (i.e., vitamin C) and CLA. Since the primary hydroxyl group is more reactive than the other hydroxyl groups, no protection of non-primary hydroxyl groups is necessary. However, one can protect non-primary hydroxyl groups prior to a condensation reaction of ascorbic acid with CLA in making the compound of formula II. Although any type of hydroxy protecting groups can be used, it is preferred that a pharmaceutically acceptable hydroxy protecting group be used. This prevents the need to remove the protecting group. Any of the methods for making tocopheryl CLA ester can be used in preparation of ascorbyl CLA ester including chemical catalyzed and enzyme catalyzed reactions.

In addition to other uses discussed above, ascorbyl CLA esters can also be used as a dietary supplement. Both ascorbic acid and CLA are dietary nutrients. Ascorbyl CLA ester is converted into ascorbic acid and CLA in the body; thus, ascorbyl CLA ester supplies both necessary dietary nutrients in one compound. The recommended amount of both ascorbic acid and CLA can be satisfied by an appropriate amount of ascorbyl CLA ester compound.

Yet another embodiment of the present invention provides a compound of the formula III:

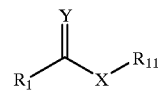

III wherein $R_{11}$ is $C_4$–$C_{30}$ conjugated polyene. Preferably, $R_{11}$ is selected from the group consisting of 3,7-dimethyl-9-(2', 6',6'-trimethylcyclohex-1'-enyl)nona-2,4,6,8-tetraenyl and 3,7-dimethyl-9-(2',6',6'-trimethylcyclohexa-1',3'-dienyl) nona-2,4,6,8-tetraenyl.

The compound of formula III can be obtained by a reaction between retinol or retinol$_2$ (i.e., vitamin A and vitamin A₂, respectively) and CLA. Any of the methods for making tocopheryl CLA ester can be used in preparation of retinyl CLA ester.

In addition to other uses discussed above, retinyl CLA esters can also be used as a dietary supplement. Both retinol and CLA are dietary nutrients. Retinyl CLA ester is converted into retinal and CLA in the body; thus, retinyl CLA ester supplies both necessary dietary nutrients in one compound. The recommended amount of both retinal and CLA can be satisfied by an appropriate amount of retinyl CLA ester compound.

Additional objects, advantages, and novel features of this invention will become apparent to those skilled in the art upon examination of the following examples thereof, which are not intended to be limiting.

EXAMPLES

Example 1

This example illustrates an enzymatic synthesis of linoleic acid ester of L-ascorbic acid (i.e., vitamin C).

A mixture of 200 mg of NOVOZYM-435 (*Candida antartica* lipase) available from Novo Nordisk Biochemical North America, Inc. (Franklinton, N.C.), 240 mg (1.36 mmol) of ascorbic acid (vitamin C) and 2.11 mL (6.8 mmol) of linoleic acid in 20 mL of 2-methyl-2-butanol was stirred at 55° C. for 8 hours. The reaction was monitored using a qualitative thin layer chromatography (TLC) using microscope plates coated with silica gel-G (Kieselgel G (Type 60), available from Brinkmann Instruments Co., Westbury, N.Y.). The TLC plates were developed using 1:4 (v/v) $CH_3OH:CHCl_3$, and components were visualized by spraying with 50% sulfuric acid and heating the sprayed TLC plate at about 105° C. for about 7 minutes. The $R_f$ of linoleic acid, monoester of ascorbic acid and ascorbic acid are approximately 0.9, 0.56 and 0.33, respectively.

The reaction mixture was filtered and the filtrate was concentrated under vacuum at a temperature of less than about 60° C. The resulting semi-solid residue was diluted with about 15 mL of diethyl ether for about 30 minutes and filtered through a filter paper. The residue was extracted once more. The ether layers were combined, dried over sodium sulfate, filtered and concentrated to yield a second semi-solid residue. Free fatty acid was removed from the second semi-solid residue by extraction with hexane (3×15 mL). The remaining second semi-solid residue was dried in a vacuum desiccator to yield about 68.5 mg (11.5% yield, based on L-ascorbic acid) of linoleic acid ester of L-ascorbic acid as about 15:85 mixture of 5- to 6-ester (as determined from proton NMR signals of H-4).

$^{13}$C NMR in DMSO-d6: δ 172.8 (C=O of linoleoyl group), and for ascorbic acid portion of the moiety: 170.5, 129.8, 127.8, 118.4, 152.3, 75.2, 65.7, and 64.5.

Example 2

This example illustrates an enzymatic synthesis of palmitic acid ester of ascorbic acid.

Using the experimental procedure of Example 1, except palmitic acid was substituted for linoleic acid, palmitic acid ester of L-ascorbic acid was prepared in 21.3% yield as about 15:85 mixture of 5- to 6-ester.

Example 3

This example illustrates the effect of the amount of lipase enzyme in the product yield.

Using the experimental procedure of Example 2 and 400 mg of the enzyme, palmitic acid ester of L-ascorbic acid was prepared in 43.5% yield as about 15:85 mixture of 5- to 6-ester.

Example 4

This example illustrates an enzymatic synthesis of palmitic acid ester of ascorbic acid.

Using the experimental procedure of Example 1, except oleic acid was substituted for linoleic acid, oleic acid ester of L-ascorbic acid was prepared in 9.9% yield as about 15:85 mixture of 5- to 6-ester.

Example 5

This example illustrates an enzymatic synthesis of 6-ascorbic acid ester of CLA.

Using the experimental procedure of Example 1, except CLA was substituted for linoleic acid, CLA ester of 6-ascorbic acid was prepared.

Examples 6–12

These examples illustrate the chemical synthesis of tocopherol-linoleate esters.

Acid chloride of linoleic acid (linoleyl chloride) was prepared in nearly a quantitative yield by reacting linoleic acid with a small excess of thionyl chloride in a solventless procedure.

The yield and reaction conditions are listed in Table 1.

TABLE 1

Chemical Synthesis of Tocopherol linoleate ester

| Example | Procedure | Yield (%) | Composition of Stripped Crude (Weight %) | | |
|---|---|---|---|---|---|
| | | | A | B | C |
| 6 | RCOOH + R'OH → (with $H_2SO_4$ catalyst) | very low | — | — | — |
| 7 | RCOCl + R'OH → (removed HCl in vacuo) | 70.7 | 80.0 | 7.6 | 4.1 |
| 8 | RCOCl + R'OH → (Mg acid acceptor) | 55.2 | 74.1 | nil | 11.4 |
| 9 | R'OH + BuLi → R'OLi R'OLi + RCOOH → | 64.6 | 89.6 | nil | 3.8 |
| 10 | RCOCL + R'OH → (pyridine cat., r.t.) | 50.5 | 71.2 | nil | 21.0 |
| 11 | RCOCL + R'OH → (pyridine cat., 55° C.) | 49.4 | 68.0 | nil | 17.9 |
| 12 | $P_2O_5$ + EtOH → $P_2O_3$(OEt)₄ $P_2O_3(OEt)_4$ + $RCO_2H$ + R'OH → | <1 | | | |

A Tocopherol linoleate ester. Calculated relative to a sample obtained by column chromatography of the product from 9. The % area of this relative standard, measured at 215 nm, was 98.5%.
B Linoleic acid.
C Tocopherol.
RCOOH = linoleic acid; RCOCl = linoleyl chloride; and R'OH = a-tocopherol Example 12 is based on a Japanese patent No. 71039687 B, which is incorporated herein in its entirety. Examples 7–11 used linoleyl chloride. It should be appreciated that dimethyl amino pyridine (DMAP) can also be added in these linoleyl chloride reactions to increase the rate of acyl transfer. Examples 10 and 11 used pyridine as an acid scavenger (i.e., acceptor), while Example 8 utilized Mg as an acid scavenger. Alternatively, as shown in Example 7, the acid (i.e., HCl) generated in the reaction can be removed by a vacuum pump. Example 9 involved converting the tocopherol to its lithium salt by reaction with butyl lithium, followed by addition of linoleyl chloride in tetrahydrofuran (THF).

Example 13

This is an example of chemically synthesizing tocopherol-CLA ester.

Acid chloride of CLA is prepared by reacting CLA with thionyl chloride without the use of any solvent. The acid chloride of CLA is then reacted with tocopherol in the presence of pyridine to provide tocopherol-CLA ester.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A compound of the formula:

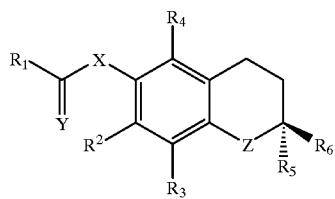

wherein X and Y are independently O, S, or $NR_7$;

Z is O or S;

$R_1$ is $C_4$–$C_{30}$ conjugated polyene;

$R_2$, $R_3$, and $R_4$, are independently hydrogen or $C_1$–$C_6$ alkyl;

$R_7$ is hydrogen, $C_1$–$C_6$ alkyl or a protecting group of an amide nitrogen, an amine nitrogen or an imine nitrogen; and $R_5$ and $R_6$ are independently hydrogen or $C_1$–$C_{20}$ alkyl.

2. The compound of claim 1, wherein X, Y and Z are O.

3. The compound of claim 2, wherein $R_5$ and $R_6$ are independently methyl or 4,8,12-trimethyltridecyl.

4. The compound of claim 3, wherein $R_2$, $R_3$, and $R_4$ are independently hydrogen or methyl.

5. The compound of claim 4, wherein $R_2$ is hydrogen.

6. The compound of claim 5, wherein $R_3$ and $R_4$ are methyl.

7. The compound of claim 5, wherein $R_3$ is methyl and $R_4$ is hydrogen.

8. The compound of claim 4, wherein $R_2$ is methyl.

9. The compound of claim 8, wherein $R_3$ and $R_4$ are methyl.

10. The compound of claim 8, wherein $R_3$ is methyl and $R_4$ is hydrogen.

11. The compound of claim 4, wherein $R_1$ is selected from the group consisting of a conjugated heptadecadienyl and a conjugated heptadecatrienyl.

12. The compound of claim 11, wherein $R_1$ is selected from the group consisting of 8,10-heptadecadienyl, 9,11-heptadecadienyl, 8,10,14-heptadecatrienyl, 9,11,14-heptadecatrienyl, and mixtures thereof.

13. The compound of claim 11, wherein $R_1$ is selected from the group consisting of (Z,E)-8,10-heptadecadienyl, (E,Z)-9,11-heptadecadienyl, (Z,E,E)-8,10,14-heptadecatrienyl, (E,Z,E)-9,11,14-heptadecatrienyl, and mixtures thereof.

14. The compound of claim 3, wherein $R_5$ is methyl and $R_6$ is 4,8,12-trimethyltridecyl.

15. The compound of claim 3, wherein $R_5$ is 4,8,12-trimethyltridecyl and $R_6$ is methyl.

16. The compound of claim 2, wherein $R_1$ is (Z,E)-8,10-heptadecadienyl, $R_2$, $R_3$, $R_4$ and $R_5$ are methyl, and $R_6$ is 4,8,12-trimethyltridecyl.

17. The compound of claim 2, wherein $R_1$ is (E,Z)-9,11-heptadecadienyl, $R_2$, $R_3$, $R_4$ and $R_5$ are methyl, and $R_6$ is 4,8,12-trimethyltridecyl.

18. A composition for topical application comprising the compound of claim 1;

and a topical carrier.

19. The composition of claim 18, wherein said to composition is a cosmetic composition.

20. The composition of claim 19, wherein said composition further comprises a sun block.

21. The composition of claim 19, wherein said composition further comprises a wax.

22. The composition of claim 18, wherein said composition is a dermatological composition.

23. The composition of claim 18, wherein said composition further comprises benzoyl peroxide.

24. The composition of claim 18, wherein said compound is a tocopheryl CLA ester.

25. The composition of claim 24, wherein said tocopheryl CLA ester is selected from the group consisting of tocopheryl 9,11-linoleate, tocopheryl 10, 12-linoleate, tocopheryl 9,11,15-linolenate, tocopheryl 10,12,15-linolenate, and mixtures thereof.

26. The composition of claim 24, wherein said tocopheryl CLA ester is selected from the group consisting of tocopheryl (Z,E)-9,11-linoleate, tocopheryl (E,Z)-10,12-linoleate, tocopheryl (Z,E,E)-9,11,15-linolenate, tocopheryl (E,Z,E)-10,12,15-linolenate, and mixtures thereof.

* * * * *